(12) United States Patent
Newland

(10) Patent No.: US 10,278,951 B1
(45) Date of Patent: May 7, 2019

(54) METHOD OF TREATING OPIATE DEPENDENCY USING TETRAHYDROCANNABINOL EXTRACTS

(71) Applicant: Jon Newland, Palm Desert, CA (US)

(72) Inventor: Jon Newland, Palm Desert, CA (US)

(*) Notice: Subject to any disclaimer, the term of this patent is extended or adjusted under 35 U.S.C. 154(b) by 0 days.

(21) Appl. No.: 15/719,851

(22) Filed: Sep. 29, 2017

Related U.S. Application Data

(60) Provisional application No. 62/401,359, filed on Sep. 29, 2016.

(51) Int. Cl.
| | |
|---|---|
| *A61K 9/00* | (2006.01) |
| *A61K 9/08* | (2006.01) |
| *A61K 47/10* | (2017.01) |
| *A61K 47/20* | (2006.01) |
| *A61K 31/352* | (2006.01) |

(52) U.S. Cl.
CPC .......... *A61K 31/352* (2013.01); *A61K 9/0053* (2013.01); *A61K 9/08* (2013.01); *A61K 47/10* (2013.01); *A61K 47/20* (2013.01)

(58) Field of Classification Search
CPC .... A61K 31/352; A61K 9/0053; A61K 47/20; A61K 9/08; A61K 47/10
USPC ........................................................ 514/454
See application file for complete search history.

(56) References Cited

U.S. PATENT DOCUMENTS

| | | | |
|---|---|---|---|
| 8,980,942 B2 * | 3/2015 | Stinchcomb | C07D 311/80 514/454 |
| 9,023,322 B2 | 5/2015 | Van Damme et al. | |
| 9,044,390 B1 * | 6/2015 | Speier | A61K 36/00 |
| 9,326,967 B2 * | 5/2016 | Perry | A61K 31/352 |
| 9,433,601 B2 | 9/2016 | Van Damme et al. | |
| 2010/0209542 A1 | 8/2010 | Boyer et al. | |
| 2012/0264818 A1 * | 10/2012 | Newland | A61K 31/353 514/454 |
| 2013/0274321 A1 * | 10/2013 | Newland | A61K 9/0019 514/454 |

FOREIGN PATENT DOCUMENTS

| | | | |
|---|---|---|---|
| WO | WO-0166089 A2 * | 9/2001 | ............. A61K 9/006 |
| WO | WO06116773 | 9/2016 | |
| WO | WO07006732 | 9/2016 | |
| WO | WO9960987 | 9/2016 | |

OTHER PUBLICATIONS

Hine et al., "Interactions Between Cannabidiol and delta.sup. 9-THC During Abstinence in Morphine-Dependent Rats", 1975, Life Sciences, 17(6), pp. 851-858. (Year: 1975).*

Edward D. French, "delta.sup.9-Tetrahydrocannabinol excites rat VTA dopamine neurons through activation of cannabinoid CB1 but not opioid receptors", 1997, Neuroscience Letters, 226(3), pp. 159-162. (Year: 1997).*

Hurd et al., "Early Phase in the Development of Cannabidiol as a Treatment for Addiction: Opioid Relapse Takes Initial Center Stage", 2015, Neurotherapeutics, 15(4), pp. 807-815. (Year: 2015).*

Edited by Rowe et al., (2009), Handbook of Pharmaceutical Excipients (6th ed.). London: APhA, (PhP) Pharmaceutical Press., pp. 238-240. (Year: 2009).*

\* cited by examiner

*Primary Examiner* — My-Chau T. Tran
(74) *Attorney, Agent, or Firm* — Mitchell A. Rossman; Terra Nova Patent Law, PLLC

(57) ABSTRACT

The present invention provides a method of orally treating opiate dependency in a patient in need thereof. The method includes: orally administering an aqueous composition including: tetrahydrocannabinol (THC); one or more aprotic solvents, for example, dimethyl sulfoxide; one or more protic solvents, for example ethanol; and water. Methods of orally reducing or preventing opiate withdrawal, orally reducing or preventing opiate withdrawal symptoms, orally treating post-surgical and chronic pain in a patient are also provided.

10 Claims, No Drawings

METHOD OF TREATING OPIATE DEPENDENCY USING TETRAHYDROCANNABINOL EXTRACTS

RELATED APPLICATIONS

This application claims priority to U.S. Provisional Patent Application Ser. No. 62/401,359, filed Sep. 29, 2016, which is hereby incorporated by reference in its entirety for all purposes.

BACKGROUND OF THE INVENTION

Drug overdose is one of the leading causes of accidental death in the United States in 2015. Opioid addiction is driving this epidemic by causing between 40,000 and 50,000 deaths a year. In 2015, approximately two million Americans had a substance abused disorder involving prescription pain relievers and about six hundred thousand Americans were addicted to heroin. Many of the heroin users started out misusing prescription painkillers.

What is needed is a non-addictive pain killer that can be used to treat opiate dependency, opiate withdrawal, and treat post-surgical and chronic pain that would eliminate these deaths.

SUMMARY OF THE INVENTION

The present invention provides a method of orally treating opiate dependency in a patient in need thereof. The method includes: orally administering an aqueous composition including: tetrahydrocannabinol (THC); one or more aprotic solvents, for example, dimethyl sulfoxide; one or more protic solvents, for example ethanol; and water. Methods of orally reducing or preventing opiate withdrawal, orally reducing or preventing opiate withdrawal symptoms, orally treating post-surgical and chronic pain in a patient are also provided.

The oral compositions may be used to treat opiate dependency, reduce or prevent opiate withdrawal, reduce or prevent opiate withdrawal symptoms, and to treat pain. In treating post-surgical and chronic pain, unlike opiates, multiple doses of the oral compositions may be administered if the first dose is not sufficient. The advantages of the oral compositions, include, for example, low toxicity, no adverse respiratory danger, no metabolic slowdown, no constipation, no slowing of wound healing, no fluid retention, and no danger of addiction.

The present invention provides a method of orally treating opiate dependency in a patient in need thereof. The method includes: orally administering an aqueous composition including: tetrahydrocannabinol (THC); one or more aprotic solvents; one or more protic solvents; and water.

In one embodiment, the opiate dependency is caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate dependency is caused by one or more opiate compounds each independently including oxycontin, hydrocodone, oxycodone, morphine, or a combination thereof.

In one embodiment, the patient is a mammal. In one embodiment, the patient is a human. In one embodiment, the one or more aprotic solvents includes dimethyl sulfoxide. In one embodiment, the dimethyl sulfoxide includes medical grade dimethyl sulfoxide. In one embodiment, the one or more protic solvents each independently includes one or more alcohols. In one embodiment, the one or more alcohols includes ethanol. In one embodiment, the one or more alcohols includes glycerol. In one embodiment, the one or more alcohols includes propylene glycol. In one embodiment, the water includes sterilized water.

In one embodiment, the aqueous composition includes tetrahydrocannabinol (THC); dimethyl sulfoxide (DMSO); ethanol; and water. In one embodiment, the aqueous composition includes; from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the aqueous composition includes: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

In one embodiment, the aqueous composition includes; about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water.

In one embodiment, the aqueous composition includes: about 2.2 weight percent (wt. %) tetrahydrocannabinol (THC); about 18.9 weight percent (wt. %) medical grade dimethyl sulfoxide (DMSO); about 39.4 weight percent (wt. %) ethanol; and about 39.4 weight percent (wt. %) water.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition further includes one or more flavoring agents, one or more sweetener agents, one or more buffering agents, one or more antioxidants, one or more preservatives, one or more preservatives, one or more pharmaceutically acceptable excipients, or combinations thereof.

The present invention provides a method of orally treating opiate dependency in a human in need thereof. The method includes: orally administering an aqueous composition including: tetrahydrocannabinol (THC); dimethyl sulfoxide (DMSO); ethanol; and water.

In one embodiment, the opiate dependency is caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate dependency is caused by one or more opiate compounds each independently including oxycontin, hydrocodone, oxycodone, morphine, or a combination thereof.

In one embodiment, the aqueous composition includes: tetrahydrocannabinol (THC); dimethyl sulfoxide (DMSO); ethanol; and water. In one embodiment, the aqueous composition consists of: tetrahydrocannabinol (THC); dimethyl sulfoxide (DMSO); ethanol; and water. In one embodiment, the aqueous composition consists essentially of: tetrahydrocannabinol (THC); dimethyl sulfoxide (DMSO); ethanol; and water.

In one embodiment, the aqueous composition includes from about 1.0 to about 10.0 weight percent (wt. %) tetrahydrocannabinol (THC). In one embodiment, the aqueous composition includes from about 10.0 to about 50.0 weight percent (wt. %) dimethyl sulfoxide (DMSO). In one embodiment, the aqueous composition includes from about 20.0 to about 60.0 weight percent (wt. %) ethanol. In one embodiment, the aqueous composition includes from about 20.0 to about 60.0 weight percent (wt. %) water.

The present invention provides a method of orally treating opiate dependency in a human in need thereof. The method includes: orally administering an aqueous composition including: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the opiate dependency is caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate dependency is caused by one or more opiate compounds each independently including oxycontin, hydrocodone, oxycodone, morphine, or a combination thereof.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition includes: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

In one embodiment, the aqueous composition includes: from about 2.3 weight percent (wt. %) tetrahydrocannabinol (THC); about 18.9 weight percent (wt. %) dimethyl sulfoxide (DMSO); about 39.4 weight percent (wt. %) ethanol; about 39.4 weight percent (wt. %) water, and wherein the opiate dependency is caused by one or more opiate compounds each independently including oxycontin, hydrocodone, oxycodone, morphine, or a combination thereof.

The present invention provides a method of orally reducing or preventing opiate withdrawal in a human in need thereof. The method includes: orally administering an aqueous composition including: tetrahydrocannabinol (THC); one or more aprotic solvents; one or more protic solvents; and water.

In one embodiment, the opiate withdrawal is caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate withdrawal is caused by one or more opiate compounds each independently including oxycontin, hydrocodone, oxycodone, morphine, or a combination thereof.

In one embodiment, the patient is a mammal. In one embodiment, the patient is a human. In one embodiment, the one or more aprotic solvents includes dimethyl sulfoxide. In one embodiment, the dimethyl sulfoxide includes medical grade dimethyl sulfoxide. In one embodiment, the one or more protic solvents each independently includes one or more alcohols. In one embodiment, the one or more alcohols includes ethanol. In one embodiment, the water includes sterilized water.

In one embodiment, the aqueous composition includes: tetrahydrocannabinol (THC); dimethyl sulfoxide (DMSO); ethanol; and water. In one embodiment, the aqueous composition consists of: tetrahydrocannabinol (THC); dimethyl sulfoxide (DMSO); ethanol; and water. In one embodiment, the aqueous composition consists essentially of: tetrahydrocannabinol (THC); dimethyl sulfoxide (DMSO); ethanol; and water.

In one embodiment, the aqueous composition includes; from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the aqueous composition includes; from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

In one embodiment, the aqueous composition includes: about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition further includes one or more flavoring agents, one or more sweetener agents, one or more buffering agents, one or more antioxidants, one or more preservatives, one or more preservatives, one or more pharmaceutically acceptable excipients, or combinations thereof.

The present invention provides a method of orally reducing or preventing opiate withdrawal in a human in need thereof. The method includes: orally administering an aqueous composition including: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the opiate withdrawal is caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate withdrawal is caused by one or more opiate compounds each independently including oxycontin, hydrocodone, oxycodone, morphine, or a combination thereof.

In one embodiment, the orally administering an aqueous composition is performed every four hours. In one embodiment, the aqueous composition is administered in a dose from about 0.5 milliliter (mL) to about 3.0 milliliter (mL).

In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition includes: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

The present invention provides a method of orally reducing or preventing opiate withdrawal in a human in need thereof. The method includes: orally administering an aqueous composition including: about 2.3 weight percent (wt. %) tetrahydrocannabinol (THC); about 18.9 weight percent (wt. %) dimethyl sulfoxide (DMSO); about 39.4 weight percent (wt. %) ethanol; about 39.4 weight percent (wt. %) water, and wherein the opiate withdrawal is caused by one or more opiate compounds each independently including oxycontin, hydrocodone, oxycodone, morphine, or a combination thereof.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

The present invention provides a method of orally reducing or preventing opiate withdrawal symptoms in a human in need thereof. The method includes: orally administering an aqueous composition including: tetrahydrocannabinol (THC); one or more aprotic solvents, one or more protic solvents; and water.

In one embodiment, the opiate withdrawal symptoms are caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate withdrawal symptoms are caused by one or more opiate compounds each independently including oxycontin, hydrocodone, oxycodone, morphine, or a combination thereof.

In one embodiment, the patient is a mammal. In one embodiment, the patient is a human. In one embodiment, the one or more aprotic solvents includes dimethyl sulfoxide. In one embodiment, the dimethyl sulfoxide includes medical grade dimethyl sulfoxide. In one embodiment, the one or more protic solvents each independently includes one or more alcohols. In one embodiment, the one or more alcohols includes ethanol. In one embodiment, the water includes sterilized water. In one embodiment, the aqueous composition includes tetrahydrocannabinol (THC); dimethyl sulfoxide (DMSO); ethanol; and water.

In one embodiment, the aqueous composition includes: tetrahydrocannabinol (THC); dimethyl sulfoxide (DMSO); ethanol; and water. In one embodiment, the aqueous composition consists of: tetrahydrocannabinol (THC); dimethyl sulfoxide (DMSO); ethanol; and water. In one embodiment, the aqueous composition consists essentially of: tetrahydrocannabinol (THC); dimethyl sulfoxide (DMSO); ethanol; and water.

In one embodiment, the aqueous composition includes; from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the aqueous composition includes; from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

In one embodiment, the aqueous composition includes: about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water.

In one embodiment, the aqueous composition includes; about 2.2 weight percent (wt. %) tetrahydrocannabinol (THC); about 18.9 weight percent (wt. %) medical grade dimethyl sulfoxide (DMSO); about 39.4 weight percent (wt. %) ethanol; and about 39.4 weight percent (wt. %) water.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition further includes one or more flavoring agents, one or more sweetener agents, one or more buffering agents, one or more antioxidants, one or more preservatives, one or more pharmaceutically acceptable excipients, or combinations thereof.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition further includes one or more flavoring agents, one or more sweetener agents, one or more buffering agents, one or more antioxidants, one or more preservatives, one or more pharmaceutically acceptable excipients, or combinations thereof.

The present invention provides a method of orally reducing or preventing opiate withdrawal symptoms in a human in need thereof. The method includes:

orally administering an aqueous composition including: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the opiate withdrawal symptoms are caused by one or more opiate compounds each independently including heroin, opium, codeine, meperidine, hydromorphone, oxycontin, hydrocodone, oxycodone, fentanyl, morphine, methadone, tramadol, or a combination thereof. In one embodiment, the opiate withdrawal symptoms are caused by one or more opiate compounds each independently including oxycontin, hydrocodone, oxycodone, morphine, or a combination thereof.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition includes: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

The present invention provides a method of orally reducing or preventing opiate withdrawal symptoms in a human in need thereof. The method includes: orally administering an aqueous composition including: about 2.3 weight percent (wt. %) tetrahydrocannabinol (THC); about 18.9 weight percent (wt. %) dimethyl sulfoxide (DMSO); about 39.4 weight percent (wt. %) ethanol; about 39.4 weight percent (wt. %) water, and wherein the opiate withdrawal symptoms are caused by one or more opiate compounds each independently including oxycontin, hydrocodone, oxycodone, morphine, or a combination thereof.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

The present invention provides a method of orally treating post-surgical and chronic pain in a patient in need thereof. The method includes: orally administering an aqueous composition including: tetrahydrocannabinol (THC); one or more aprotic solvents; one or more protic solvents; and water.

In one embodiment, the patient is a mammal. In one embodiment, the patient is a human.

In one embodiment, the one or more aprotic solvents includes dimethyl sulfoxide. In one embodiment, the dimethyl sulfoxide includes medical grade dimethyl sulfoxide. In one embodiment, the one or more protic solvents each independently includes one or more alcohols. In one embodiment, the one or more alcohols includes ethanol. In one embodiment, the water includes sterilized water.

In one embodiment, the aqueous composition includes: tetrahydrocannabinol (THC); dimethyl sulfoxide (DMSO); ethanol; and water. In one embodiment, the aqueous composition consists of: tetrahydrocannabinol (THC); dimethyl sulfoxide (DMSO); ethanol; and water. In one embodiment, the aqueous composition consists essentially of: tetrahydrocannabinol (THC); dimethyl sulfoxide (DMSO); ethanol; and water.

In one embodiment, the aqueous composition includes: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the aqueous composition includes: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

In one embodiment, the aqueous composition includes; about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition further includes one or more flavoring agents, one or more sweetener agents, one or more buffering agents, one or more antioxidants, one or more preservatives, one or more pharmaceutically acceptable excipients, or combinations thereof.

The present invention provides a method of orally treating post-surgical and chronic pain in a human in need thereof. The method includes: orally administering an aqueous composition including: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water.

In one embodiment, the orally administering an aqueous composition is performed every four hours. In one embodiment, the aqueous composition is administered in a dose from about 0.5 milliliter (mL) to about 3.0 milliliter (mL). In one embodiment, the aqueous composition is administered in a dose from about 1.0 milliliter (mL) to about 2.0 milliliter (mL). In one embodiment, the aqueous composition is administered in a dose about 1.5 milliliter (mL).

In one embodiment, the aqueous composition includes: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water.

In one embodiment, the aqueous composition includes: about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water.

The present invention also provides a therapeutic kit including: an aqueous composition including: tetrahydrocannabinol (THC); one or more aprotic solvents; one or more protic solvents; and water; and instructions for the use of the oral composition and dosage regime thereto.

The present invention also provides a therapeutic kit including: an aqueous composition including: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water; and instructions for the use of the oral composition and dosage regime thereto.

The present invention also provides a therapeutic kit including: an aqueous composition including: from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water; and instructions for the use of the oral composition and dosage regime thereto.

The present invention also provides a therapeutic kit including: an aqueous composition including: about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water; and instructions for the use of the oral composition and dosage regime thereto.

DETAILED DESCRIPTION OF THE INVENTION

The present invention provides a method of orally treating opiate dependency in a patient in need thereof. The method includes: orally administering an aqueous composition including: tetrahydrocannabinol (THC); one or more aprotic solvents, for example, dimethyl sulfoxide; one or more protic solvents, for example ethanol; and water. Methods of orally reducing or preventing opiate withdrawal, orally reducing or preventing opiate withdrawal symptoms, orally treating post-surgical and chronic pain in a patient are also provided.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *The American Heritage Dictionary of the English Language*, Houghton Mifflin, Boston Mass., 1981.

One of ordinary skill in the art would readily appreciate that the pharmaceutical compositions and methods described herein can be prepared and practiced by applying known procedures in the pharmaceutical arts. These include, for example, unless otherwise indicated, conventional techniques of pharmaceutical sciences including pharmaceutical dosage form design, drug development, pharmacology, of organic chemistry, and polymer sciences. See generally, for example, *Remington: The Science and Practice of Pharmacy*, 21$^{st}$ edition. Lippincott, Williams & Wilkins, (2005).

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example, about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the phrase "acute pain" refers to any persistent pain of less than six (6) months' duration.

As used herein, the term "agent" refers to anything that may have an impact on any living system such as a cell, nerve or tissue. For examples, the agent can be a chemical agent. The agent can also be a biological agent. The agent may include at least one known component. The agent can also be a physical agent.

As used herein, the term "administration" refers to a method of placing a device to a desired site. The placing of a device can be by any pharmaceutically accepted means such as by swallowing, retaining it within the mouth until the drug has been dispensed, placing it within the buccal cavity, inserting, implanting, attaching, etc. These and other methods of administration are known in the art.

As used herein, the phrase "aprotic solvent" refers to polar solvents of moderately high dielectric constant which do not contain acidic hydrogen. Examples of common aprotic solvents are dimethylsulfoxide (DMSO), dimethylformamide, sulfolane, tetrahydrofuran, diethyl ether, methyl-t-butyl ether, or 1,2-dimethoxyethane.

As used herein, the phrase "aqueous composition" refers to a liquid composition composed, but not necessarily exclusively, of water. Other components may also be present, such as salts, co-solvents, buffers, stabilizers, dispersants, colorants and the like.

As used herein, the phrase "at risk for" refers to a medical condition or set of medical conditions exhibited by a patient which may predispose the patient to a particular disease or affliction.

As used herein, the term "bioavailability" refers to the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

As used herein, the term "biocompatible" refers to the material, substance, compound, molecule, polymer, or system, which does not cause severe toxicity, severe adverse biological reaction, or lethality in an animal when administered at reasonable doses and rates.

As used herein, the phrase "chronic pain" refers to any persistent pain of greater than six (6) months' duration.

As used herein, the term "comprising" or "comprises" is intended to mean that the compositions and methods include the recited elements, but not excluding others.

As used herein, the phrase "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the phrase "consisting of" shall mean excluding more than trace elements of other ingredients and substantial method steps.

As used herein, the terms "consisting essentially of" and "consisting of" are embodied in the term "comprising."

As used herein, the term "delivery" refers to the release of a drug from a device comprising that drug into an environment surrounding the device. The environment into which the drug so released may or may not be the ultimate site of activity for that drug. In some instances, the released drug may need to be transported to its ultimate site of activity.

As used herein, the phrase "dosage form" refers to a physical and chemical composition of an active pharmaceutical ingredient (API) that is adapted for administration to a patient in need thereof. The inventive dosage form is a liquid.

As used herein, the phrase "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

As used herein, the terms "include." "for example," "such as," and the like are used illustratively and are not intended to limit the present invention.

As used herein, the terms "individual." "host." "subject," and "patient" are used interchangeably, and refer to a mammal, including, but not limited to, primates, including simians and humans.

As used herein, the terms "invention," "the invention," "this invention." "the present invention" and "disclosure" are intended to refer broadly to all of the subject matter of this patent and the patent claims below. Statements containing these terms should be understood not to limit the subject matter described herein or to limit the meaning or scope of the patent claims below. The subject matter should be understood by reference to appropriate portions of the entire specification of this patent, any or all drawings and each claim.

As used herein, the terms "individual," "host," "subject," and "patient" are used interchangeably, and refer to a mammal, including, but not limited to, primates, including simians and humans.

As used herein, the term "liquid" refers to a substance that undergoes continuous deformation under a shearing stress. See, e.g., *Concise Chemical and Technical Dictionary*, 4$^{th}$ Edition, Chemical Publishing Co., Inc., p. 707, New York, N.Y. (1986).

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, such as horses, cattle, sheep, and goats, and research and domestic species, including dogs, cats, mice, rats, guinea pigs, and rabbits.

As used herein, the phrase "medical grade" refers to a material that may be used in medical applications.

As used herein, the phrase "opiate compound" refers to any compound having a morphine-based ring structure such that the structure-activity relationships of the compound results in physiological binding affinity to an opiate receptor. Opiate compounds may include, for example, heroin, opium, codeine, meperidine, hydromorphone, oxycontin, hydrocodone, oxycodone, fentanyl, morphine, methadone, tramadol, and the like.

As used herein, the terms "optional" or "optionally" mean that the subsequently described event or condition may need not occur, and that the description includes instances where the event or condition occurs and instances in which it does not.

As used herein, the phrase "oral administration" or "orally" refers to the introduction of a pharmaceutical composition into a subject by way of the oral cavity (e.g., in aqueous liquid or solid form).

As used herein, the term "patient" refers to a warm-blooded animal, and preferably a mammal, for example, a cat, dog, horse, cow, pig, mouse, rat, or primate, including a human.

As used herein, the phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as *The United States Pharmacopeia* describe the analytical criteria to assess the pharmaceutical acceptability of numerous ingredients of interest.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the phrase "protic solvent" refers to a solvent containing hydrogen that is attached to oxygen, and hence is appreciably acidic. Common protic solvents include such solvents as water, methanol, ethanol, 2-propanol, and 1-butanol.

As used herein, the phrase "repeatedly exposed" refers to the administration of an addictive drug or compound to a subject on a regular schedule for a prolonged period of time. Such a schedule may comprise administration of a dose ranging between approximately once-to-twelve times per day for a time period lasting at least two successive days and may range over weeks, months, years, and even decades.

As used herein, the phrase "single dosage" refers to a pharmaceutical composition of a composition that is capable of achieving its intended effect in a single application or administration (e.g. Once a day).

As used herein, the term "subject" refers to a human or animal.

As used herein, the phrase "substitute for" refers to switching the administration of a first compound or drug to a subject for a second compound or drug to the subject.

As used herein, the term "tetrahydrocannabinol (THC)" refers to Δ-9 tetrahydrocannabinol (THC) with the IPUAC name (−)-(6aR,10aR)-6,6,9-trimethyl-3-pentyl-6a,7,8,10a-tetrahy dro-6H-benzo[c]-chromen-1-ol).

As used herein, the terms "therapy," and "therapeutic" refer to either "treatment" or "prevention," thus, agents that either treat damage or prevent damage are "therapeutic."

As used herein, the term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells which line hollow organs or body cavities).

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

As used herein, the term "treatment," covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, the phrase "weight percent (wt. %)" refers to the percentage of a component relative to the total weight of the composition.

As used herein, the term "withdrawal" refers to any of the predictable signs and symptoms resulting from abrupt removal of, or a rapid decrease in the regular dosage of an opioid.

As used herein, the terms "µg" denotes microgram. "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar, and "nm" denotes nanometer.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible sub ranges as well as individual numerical values within that range. For example, description of a range such as 1% to 8% should be considered to have specifically disclosed sub ranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

The present invention provides methods of orally treating opiate dependency, orally reducing or preventing opiate withdrawal, and orally reducing or preventing opiate withdrawal symptoms in a patient in need thereof. The methods include: orally administering an aqueous composition including: tetrahydrocannabinol (THC); one or more aprotic solvents; one or more protic solvents; and water.

Preferably, the tetrahydrocannabinol (THC) was prepared by using a commercial *cannabis* extract (Croc Tears, from Doc Croc LLC, WA), assayed at 92.6% tetrahydrocannabinol (THC), 5.28% tetrahydrocannabinolic acid (THCA), and 2.02% cannabinol (CBN) content and produced from a Butane Hash Oil (BHO) base, winterized and distilled using short path fractional distillation to remove fats, lipids, waxes, terpenes and other impurities and decarboxylated to convert tetrahydrocannabinolic acid (THCA) to Δ-9 tetrahydrocannabinol (THC), enabling attachment to $CB_1$ and $CB_2$ receptors. Preferably, the composition is prepared by dissolving the tetrahydrocannabinol (THC)) extract in medical grade dimethyl sulfoxide (DMSO) followed by addition of aqueous ethanol.

Typically, the opiate dependency is caused by one or more opiate compounds including, for example, heroin, opium, codeine, meperidine, hydromorphone, oxycontin, hydrocodone, oxycodone, fentanyl, morphine, methadone, tramadol, or a combination thereof. Preferably, the opiate dependency is caused by one or more opiate compounds each independently including oxycontin, hydrocodone, oxycodone, morphine, or a combination thereof.

Preferably, the patient is a mammal, for example, a human.

Preferably, the one or more aprotic solvents include acetonitrile, dimethyl formamide, dimethyl sulfoxide, or combinations thereof, and more preferably, the one or more aprotic solvents include dimethyl sulfoxide. Preferably, the dimethyl sulfoxide is medical or pharmaceutical grade. Preferably, the one or more protic solvents are one or more alcohols. Preferably, the one or more alcohols is ethanol. Preferably, the ethanol is 150-proof.

Preferably, the aqueous composition includes tetrahydrocannabinol (THC); dimethyl sulfoxide (DMSO); ethanol; and water, more preferably, the aqueous composition includes: from about 1.0 to about 10.0 weight percent (wt. %) tetrahydrocannabinol (THC); from about 10.0 to about 50.0 weight percent (wt. %) dimethyl sulfoxide (DMSO); from about 20.0 to about 60.0 weight percent (wt. %) ethanol; and from about 20.0 to about 60.0 weight percent (wt. %) water, yet more preferably, the aqueous composition includes; from about 2.0 to about 3.0 weight percent (wt. %) tetrahydrocannabinol (THC); from about 15.0 to about 25.0 weight percent (wt. %) dimethyl sulfoxide (DMSO); from about 35.0 to about 45 weight percent (wt. %) ethanol; and from about 35.0 to about 45.0 weight percent (wt. %) water, and most preferably, the aqueous composition includes; about 2.3 weight percent (wt. %) tetrahydrocannabinol (THC); about 18.9 weight percent (wt. %) dimethyl sulfoxide (DMSO); about 39.4 weight percent (wt. %) ethanol; and about 39.4 weight percent (wt. %) water.

Preferably, the orally administering an aqueous composition is performed every four hours. Preferably, the aqueous composition is administered in a dose from about 0.5 milliliter (mL) to about 3.0 milliliter (mL), more preferably, the aqueous composition is administered in a dose from about 1.0 milliliter (mL) to about 2.0 milliliter (mL), and most preferably, the aqueous composition is administered in a dose about 1.5 milliliter (mL).

The aqueous composition may further include other optional ingredients, for example, one or more flavoring agents, one or more sweetener agents, one or more buffering agents, one or more antioxidants, one or more preservatives, one or more pharmaceutically acceptable excipients, and the like, or combinations thereof.

Suitable flavoring agents may include, for example, menthol flavor, *eucalyptus*, mint flavor, and the like, or combinations thereof. The amount of the one or more flavoring agents may be, for example, from about 0.5 weight percent (wt. %) to about 12 weight percent (wt. %), based on the total weight of the aqueous composition.

Suitable sweetener agents may include, for example, natural sweeteners, for example, xylitol, sorbitol, isomalt, and the like, or combinations thereof; and artificial sweeteners, for example, aspartame, sucralose, acesulfame potassium, saccharin, and the like, or combinations thereof. The amount of the one or more sweetener agents may be, for example, at least about 0.05 weight percent (wt. %) based on the total weight of the aqueous composition.

Suitable buffering agents may include, for example, acetates, glycinates, phosphates, glycerophosphates, citrates and the like, or combinations thereof. The amount of the one or more buffering agents may be, for example, from about 0.5 to about 5 weight percent (wt. %) based on the total weight of the aqueous composition.

Suitable anti-oxidants may include, for example, ascorbyl palmitate, sodium ascorbate, and the like, or combinations thereof. The amount of the one or more antioxidants may be, for example, from about 0.05 to about 0.3 weight percent (wt. %) based on the total weight of the aqueous composition.

Suitable pharmaceutically acceptable excipients may include, for example, fillers, binders, lubricants, and the like, or combinations thereof.

Typically, the one or more optional ingredients, if present, are present in an amount of about 0.001% to about 30%, about 3% to about 25%, or about 5% to about 15%, by weight. Illustratively, one or more emollients are present in a total amount of about 0.001%, about 0.25%, about 0.5%, about 0.75%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight percent.

The aqueous compositions, as described herein, may be given in a single administration or in multiple administrations. The aqueous compositions are orally given for at least one day, at least two days, at least three days, at least four days, at least 5 days, once a week, at least twice a week, at least once a day, at least twice a day, multiple times daily, multiple times weekly, biweekly, at least once a month, or any combination thereof.

The aqueous compositions, as described herein, may be orally given for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years.

Preferably, the aqueous composition is given orally until the pain, the opiate dependency, or a combination thereof subsides. The aqueous composition is preferably administered six times a day for from one day to a week or more until the pain, the opiate dependency, or a combination thereof subsides.

Typically, the oral composition may be used to treat, for example, chronic and acute pain and post-surgical pain It will be understood that, although the terms first, second, etc. May be used herein to describe various elements, these elements should not be limited by these terms. These terms are only used to distinguish one element from another. For example, a first element could be termed a second element, and, similarly, a second element could be termed a first element without departing from the teachings of the disclosure.

The invention illustratively disclosed herein suitably may be practiced in the absence of any element which is not specifically disclosed herein.

EXAMPLES

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Example 1

Composition of *Cannabis* Extract

An oral composition oftetrahydrocannabinol (THC) was prepared by using a commercial *cannabis* extract from a licensed manufacturer (Croc Tears, from Doc Croc LLC, WA), assayed at 92.6% tetrahydrocannabinol (THC), 5.28% tetrahydrocannabinolic acid (THCA), and 2.02% cannabinol (CBN) content and produced from a Butane Hash Oil (BHO) base, winterized and distilled using short path fractional distillation to remove fats, lipids, waxes, terpenes and other impurities and decarboxylated to convert tetrahydrocannabinolic acid (THCA) to $\Delta$-9 tetrahydrocannabinol (THC), enabling attachment to $CB_1$ and $CB_2$ receptors.

For the preparation of the composition, 0.9 milliliter (mL) (equivalent to 0.926 grams tetrahydrocannabinol (THC)) of the extract was dissolved in 7.7 grams (equivalent to 7.0 milliliter (mL)) medical grade dimethyl sulfoxide (DMSO)

followed by addition of 32.1 grams (equivalent to 38.2 milliliter (mL)) 150 proof ethanol giving a 46.1 milliliter (mL) final volume with 20 mg/mL tetrahydrocannabinol (THC), 1.14 mg/mL tetrahydrocannabinolic acid (THCA) and. 436 mg/mL cannabinol (CBN) concentration. The composition was provided in 2-ounce amber glass bottles with a dropper and a label containing dosing instructions and warning information.

Example 2

Exemplary Protocol for Acute and Chronic Pain Management and Opiate Dependency

All study participants had their health history reviewed, were 21 years of age or older, did not take any other marijuana based product during the drug trial, were not pregnant, had no known liver or kidney disease, were not being treated for depression or have any other mental health concerns, had no known allergies to marijuana and had a medically recognized condition for which narcotic pain relief was anticipated, i.e. Acute post-operative/injury pain, chronic neuropathic/cancer pain or palliative end of life issues.

The following protocol was followed by the study participant:

(1) Started the initial dose at 1.5 milliliter (mL), elderly patients started with 0.5-1 milliliter (mL). This was mixed with a small drink or juice if desired.

(2) Repeat in 1 hour if effects are minimum.

(3) Adjust the dose of 1-4 milliliter (mL) to the participant's requirements for pain control.

(4) Effects should last 4-6 hours but frequently up to 12 hours of pain relief will be noted. Repeat as needed every 4 plus hours.

(5) Fill medication data worksheet out for each dose taken. While participating in the study, the participants can not drink alcohol, drive a vehicle or work near machinery. Tasks or making decisions requiring full mental attention should be avoided.

Trial length may be approximately 1-2 weeks for acute or chronic pain volunteers. Chronic pain patients and experienced marijuana user may require greater than average composition doses. Some possible side effects of the composition may include, for example, allergic reaction, dizziness, drowsiness, mental impairment, dry mouth, dry eyes, change in blood pressure and heart rate, anxiety and/or paranoia, dependence, depression and/or euphoria, and prolonged effect.

Example 3

Pain Management Study Results

Nine volunteer patients (5 males between 51 and 79 years old and 4 females between 49 and 67 years old) with pain due to various medical conditions were enrolled in the study. A summary of the patient experiences is provided below. A pain score was defined as: 0=no pain, 5=moderate, 9 and above=side effects outweighing advantages of a pain medicine.

Patient 1. This patient was a 58-year-old male. The patient suffered work-related injury as a tree trimmer. He has had spine surgery and currently had multiple disk herniation and constant pain. The individual had taken opioids (e.g., NORCO or Hydrocodone bitartrate/acetaminophen 10/235 at 2 per day)) daily for about 5 to about 6 years, about 20 mg/day currently. He had a pain score of about 7 initially. The patient was able to forego use of opioids for two days, at which time he left the trial on the advice of the orthopedic knee surgeon. The surgeon wanted him to take only prescription anti-inflammatory. In two days, the patient felt pain free.

Patient 2. This patient was a 51-year-old male. This patient had a complex and difficult medical situation, due to traumatic spine injury eight years ago, and had been taking several medications each day, including opioids (e.g., EXALGO or Hydromorphone Hydrochloride; about 56 mg/day). This individual was bed ridden most of the day and mobile only by using an electric wheelchair. He used about 260 Morphine Equivalent Doses or more per day. Prior to starting the composition, the patient had a pain score of 10. He reported that the composition dramatically improved pain management, including reducing pain score of 10+ to zero while dosed. The patient did not show narcotic withdrawal signs.

Patient 3. This patient was a 66-year-old male. The patient had a pain score of 5 (forearms to hands and calves to feet) due to very aggressive multiple sessions of chemotherapy as a result of stage IV lymphoma. The patient was not taking opioids; however, the patient had used a USP ethanol tincture of *cannabis* preparation as a sleep aid for over a year and the use was discontinued to participate in the trial. The patient reported that the composition substantially improved pain management, muscle restlessness and ability to sleep, and noticeably improved edema.

Patient 4. This patient was a 79-year-old male who had moderate left knee pain following surgery, which he treated with over the counter medications with limited success. During the trial, he received significant pain relief while on the composition. The evening dose was usually followed by sleep. The day time dosing was followed by some dizziness and confusion. Dosages ranged from about 1 milliliter (mL) to about 1.5 milliliter (mL).

Patient 5. This patient was a 66-year-old male who significant knee pain as a result of sports injuries. During the trial, he took about 1 to about 2 milliliter (mL) of the composition, with best pain relief from about 2 milliliter (mL), although he experienced euphoric effects at that dose. The patient felt sleepy and drowsiness at times.

Patient 6. This patient is a 66-year-old female. The patient was using opioids for over four years due to orthopedic trauma and subsequent surgery resulting from an accident. Over the course of two weeks, the patient was able to substitute the composition for NORCO (e.g., hydrocodone bitartrate/acetaminophen), substantially improving pain management and ability to sleep.

Patient 7. This patient is a 49-year-old female. This patient suffered catastrophic injury as a result of a student assault at work. The individual had traumatic brain injury, blindness in one eye, deafness in one ear, reconstructed orbital socket, reconstructed nose with bone graft, non-vital anterior teeth, crush injury to hand and more. For about four years, this patient had been taking about 10-80 mg/day Morphine equivalent doses, currently hydrocodone. Prior to the initial dose of the composition, the patient had pain score of 7. After taking a first dose of about 1.5 milliliter (mL), the pain was reduced to a pain score of 0 and 2 after about 2 and about 4 hrs., respectively. The patient was able to replace opioid use for two weeks while on the trial, with excellent pain management and added benefit of increased cognitive ability to read books, good sleeping, even about 15 pounds of weight reduction and was more reactive. Reported side effect was nausea.

Patient 8. This patient is a 64-year-old female. She had a total knee replacement a year ago. At that time, she took about 10 mg OxyContin twice daily and about 10 mg Oxycodone every 3 hours for 2 weeks. This year she underwent a total knee replacement on her other knee and achieved a pain score of 4 before utilizing the composition. After taking about 2 milliliter (mL) of the composition initially, the pain was reduced to a pain score of 2 and 1, within about 1 and about 2 hrs., respectively. After using the composition about 1 to about 3 times a day, she experienced good pain relief after about 3 days and could participate in exercise. Exercise intensity was increased after about 5 days. Initial side effects were feeling sleepy.

Patient 9. This patient is a 67-year-old female with metastatic breast cancer, bone pain, and neuropathy. Her goal was to achieve enough relief to sleep. During the trial, she took about 1 milliliter (mL) at bedtime and obtained significant pain relief, allowing her to obtain a restful sleep. The patient felt dizzy and high; however, most nights she was able to fall sleep without much pain and felt pain free in the morning.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B. C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance or component fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicant reserves the right to physically incorporate into this specification any and all materials and information from any such patents, applications, publications, scientific articles, web sites, electronically available information, and other referenced materials or documents. Applicant reserves the right to physically incorporate into any part of this document, including any part of the written description, the claims referred to above including but not limited to any original claims.

What is claimed is:

1. A method of orally treating opiate dependency in a human in need thereof comprising;
   orally administering an aqueous composition consisting essentially of:
   tetrahydrocannabinol (THC);
   dimethyl sulfoxide (DMSO);
   ethanol; and
   water.

2. The method of claim 1, wherein the opiate dependency is caused by one or more opiate compounds each independently comprising oxycontin, hydrocodone, oxycodone, morphine, or a combination thereof.

3. The method of claim 1, wherein the aqueous composition consists essentially of:
   from about 1.0 to about 10.0 weight percent (wt. %) tetrahydrocannabinol (THC);
   from about 10.0 to about 50.0 weight percent (wt. %) dimethyl sulfoxide (DMSO);
   from about 20.0 to about 60.0 weight percent (wt. %) ethanol; and
   from about 20.0 to about 60.0 weight percent (wt. %) water.

4. The method of claim 1, wherein the orally administering an aqueous composition is performed every four hours.

5. The method of claim 1, wherein the aqueous composition is administered in a dose from about 0.5 milliliter (mL) to about 3.0 milliliter (mL).

6. The method of claim 1, wherein the aqueous composition is mixed with a drink or juice prior to oral administration.

7. A method of orally treating opiate dependency in a human in need thereof comprising;
   orally administering an aqueous composition consisting essentially of:
   tetrahydrocannabinol (THC);
   dimethyl sulfoxide (DMSO);
   ethanol; and
   water, and
   wherein the opiate dependency is caused by one or more opiate compounds each independently comprising oxycontin, hydrocodone, oxycodone, morphine, or a combination thereof.

8. The method of claim 7, wherein the orally administering an aqueous composition is performed every four hours.

9. The method of claim 7, wherein the aqueous composition is administered in a dose from about 0.5 milliliter (mL) to about 3.0 milliliter (mL).

10. The method of claim 7, wherein the aqueous composition is mixed with a drink or juice prior to oral administration.

* * * * *